(12) United States Patent
Hartlep et al.

(10) Patent No.: US 8,688,239 B2
(45) Date of Patent: Apr. 1, 2014

(54) ELECTRODE ARRANGEMENT

(71) Applicant: Cerbomed GmbH, Erlangen (DE)

(72) Inventors: Andreas Hartlep, Holzkirchen (DE);
Christoph Beck, Moehrendorf (DE);
Stefan Baer, Cadolzburg (DE)

(73) Assignee: Cerbomed GmbH, Erlangen (DE)

( * ) Notice: Subject to any disclaimer, the term of this patent is extended or adjusted under 35 U.S.C. 154(b) by 0 days.

(21) Appl. No.: 13/782,135

(22) Filed: Mar. 1, 2013

(65) Prior Publication Data
US 2013/0231730 A1    Sep. 5, 2013

Related U.S. Application Data

(60) Provisional application No. 61/681,198, filed on Aug. 9, 2012.

(30) Foreign Application Priority Data

Mar. 2, 2012  (DE) .......................... 10 2012 004 021
Jul. 25, 2012  (DE) .......................... 10 2012 014 764

(51) Int. Cl.
*A61N 1/04*    (2006.01)

(52) U.S. Cl.
USPC .............................. 607/136; 607/139; 607/57

(58) Field of Classification Search
USPC .......... 607/55, 56, 57, 136, 137, 139; 600/25; 381/312; 181/129, 130
See application file for complete search history.

(56) References Cited

U.S. PATENT DOCUMENTS

| 5,514,175 A | 5/1996 | Kim et al. |
| 5,999,859 A * | 12/1999 | Jolly .............................. 607/137 |
| 2011/0166624 A1 * | 7/2011 | Dietrich et al. ................. 607/57 |

FOREIGN PATENT DOCUMENTS

| DE | 10 2005 003 735 A1 | 7/2006 |
| EP | 2 026 872 | 2/2009 |

* cited by examiner

*Primary Examiner* — Christopher D Koharski
*Assistant Examiner* — Michael Carey
(74) *Attorney, Agent, or Firm* — Lucas & Mercanti, LLP

(57) ABSTRACT

The invention relates to an electrode arrangement for applying of a transcutaneous electrical stimulation stimulus onto the surface of a section of the human ear, which comprises a holding element to be attached at or in the ear as well as at least one electrode, which electrode is arranged in or at an electrode carrier, wherein the holding element comprises a linear guide in which a supporting rod is arranged linear movable in the direction of a longitudinal axis (L) of the holding element and wherein the electrode carrier is arranged at the supporting rod. To obtain an improved transcutaneous stimulation the invention proposes that the electrode carrier comprises at least one carrier section on which the electrode is arranged, wherein the electrode comprises at least one cylindrical and/or spherical segment shaped and/or conical surface section.

13 Claims, 15 Drawing Sheets

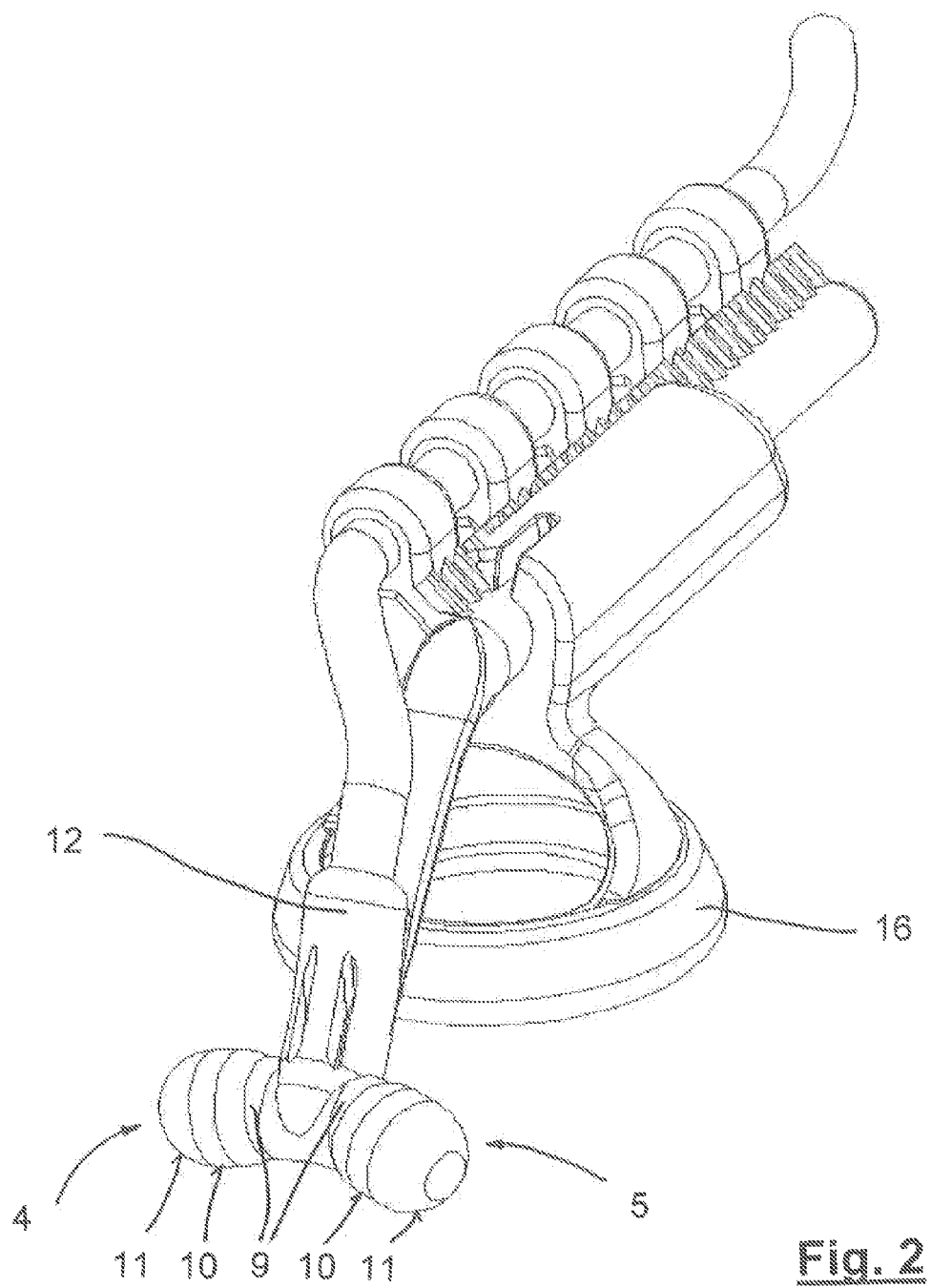

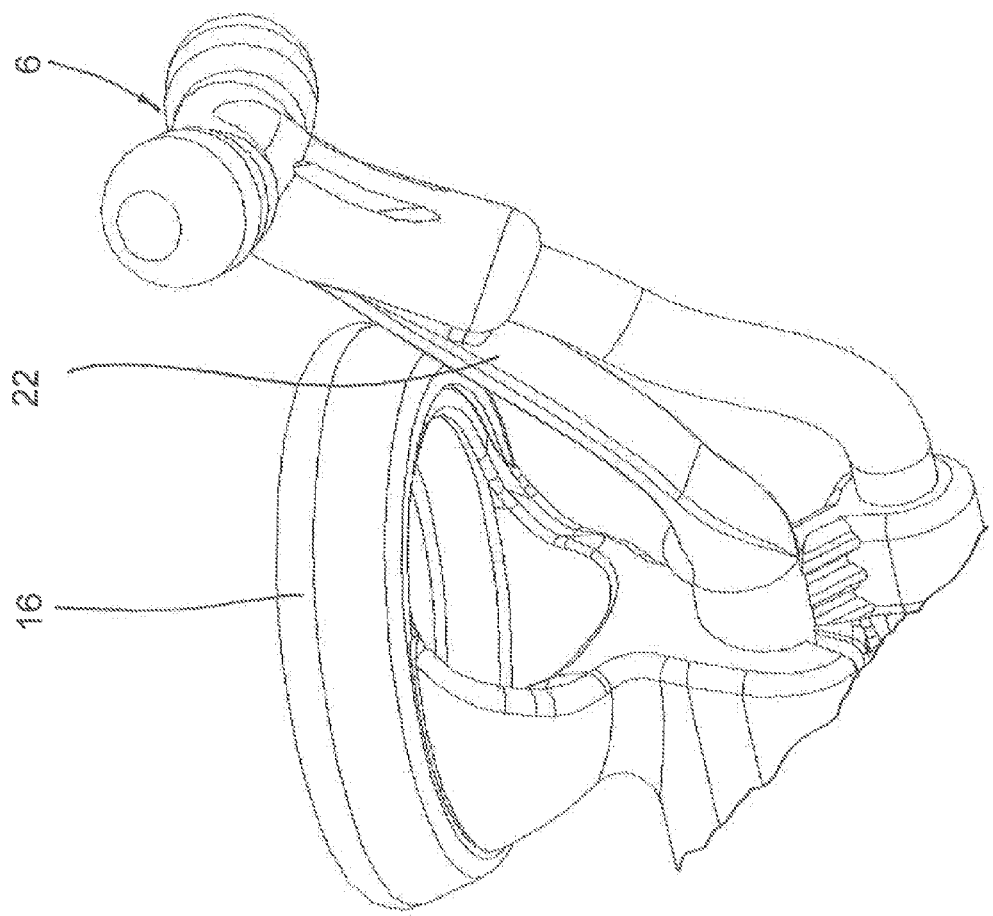

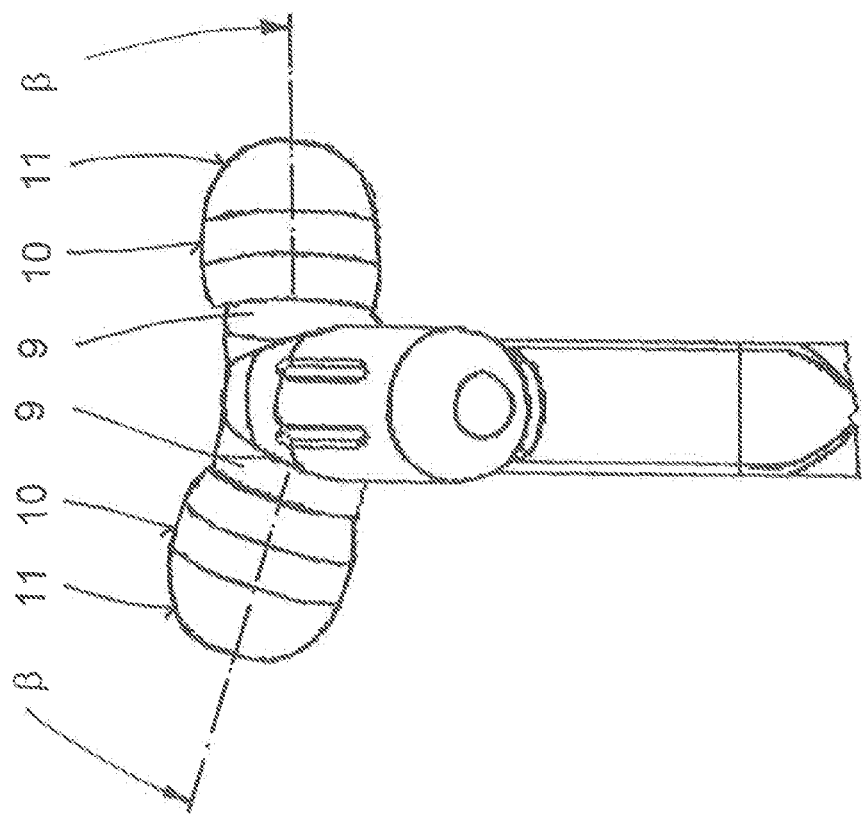

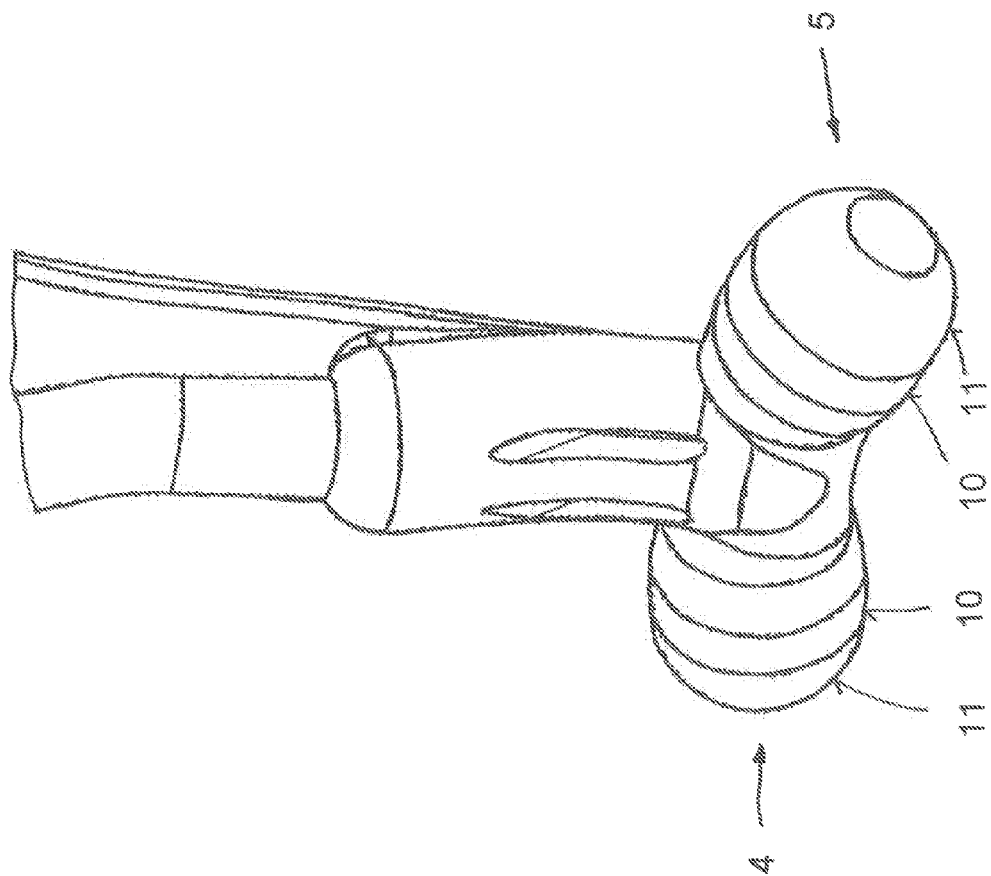

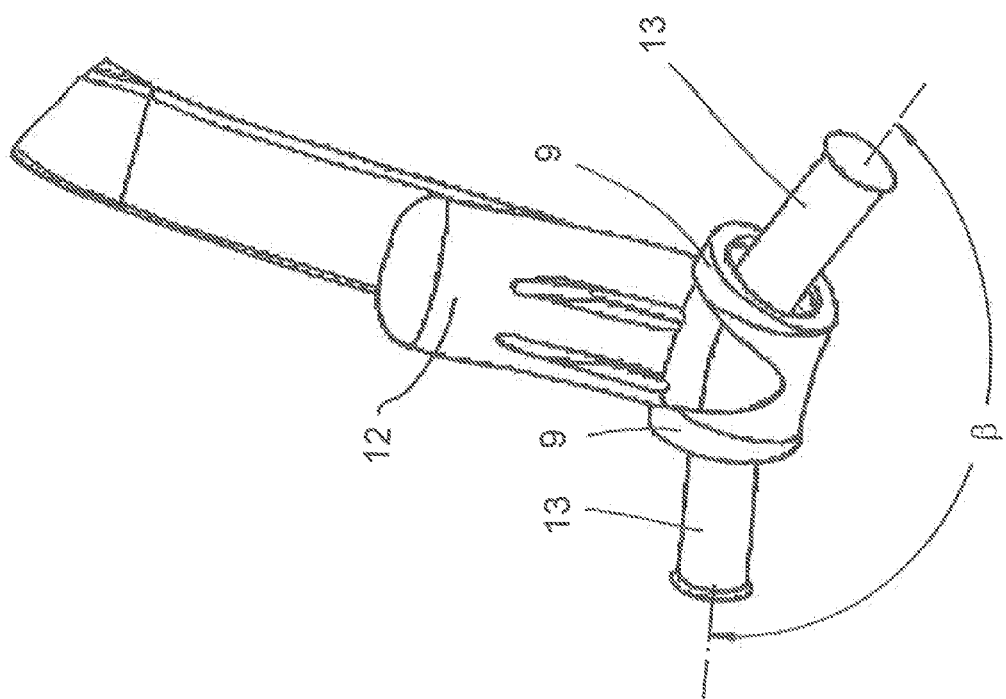

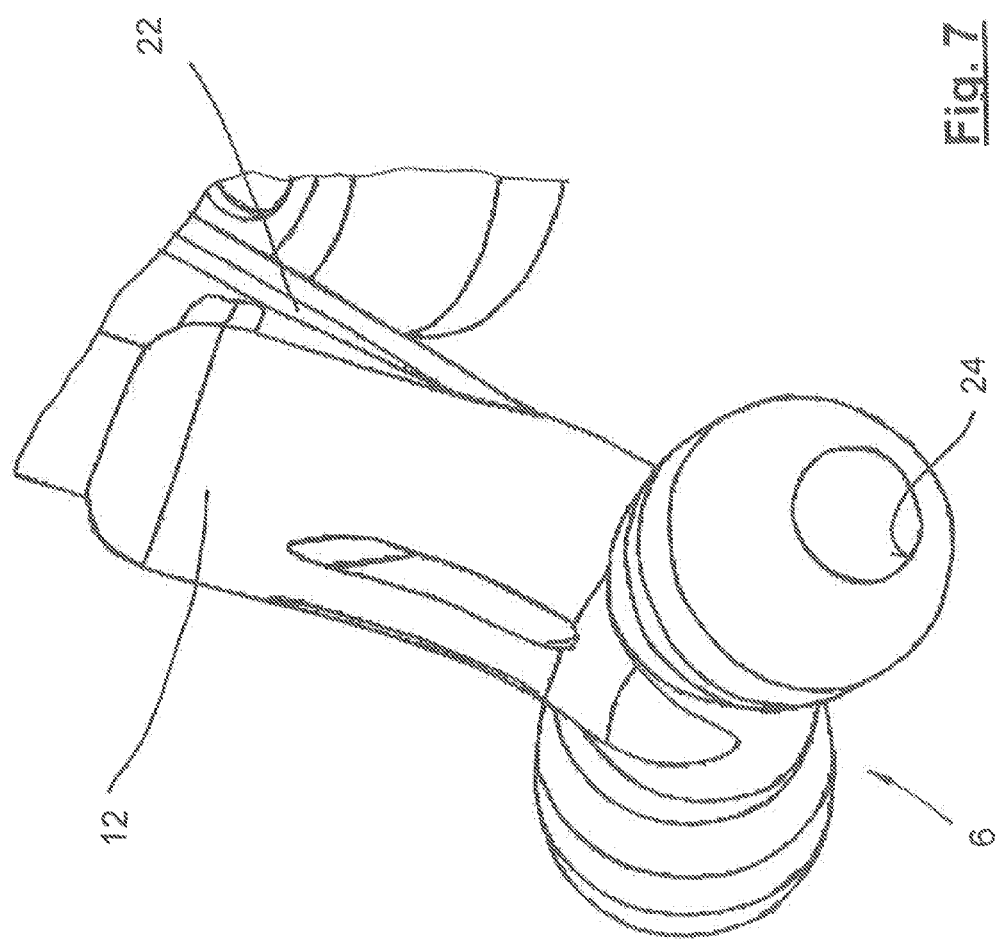

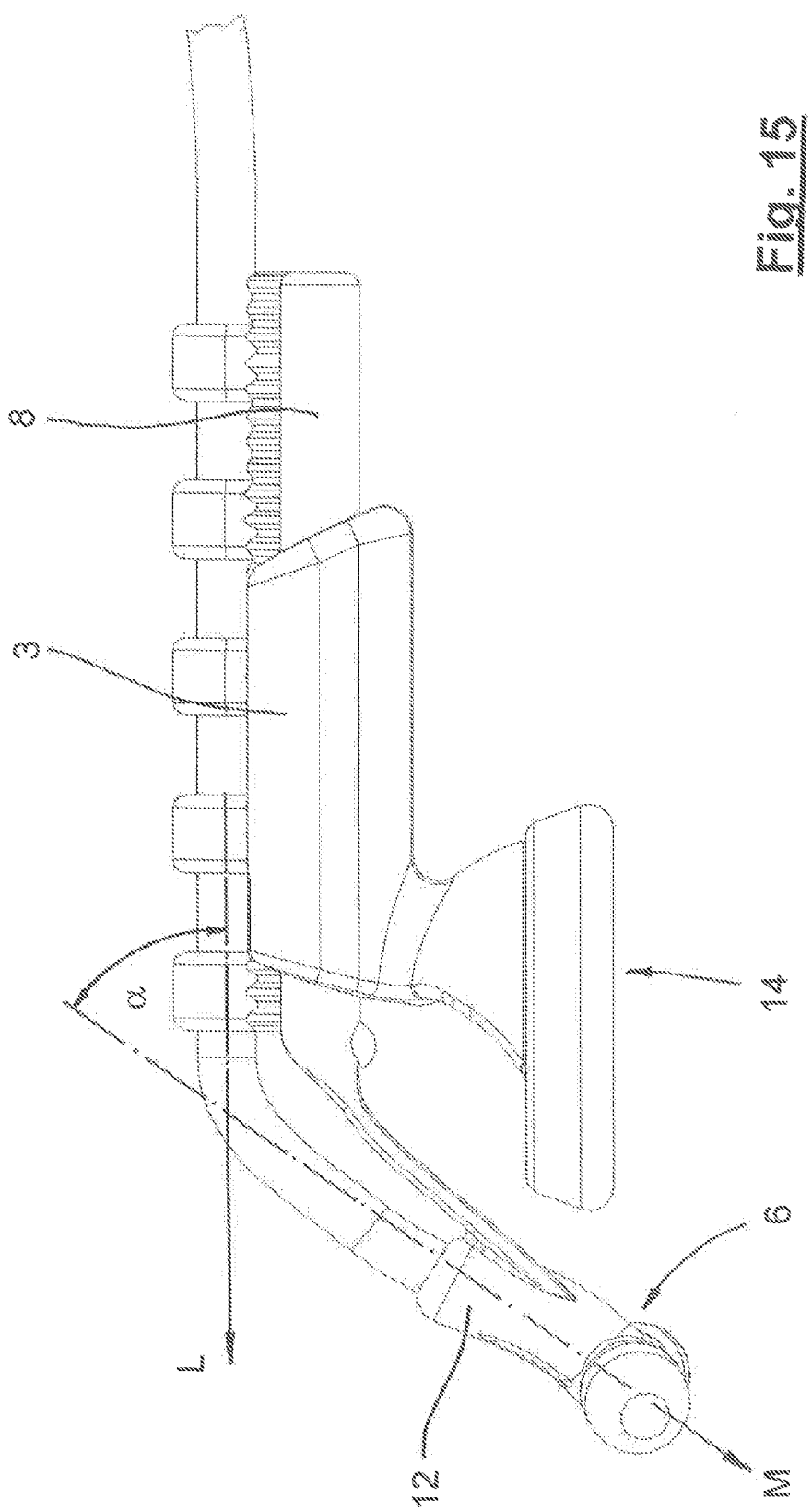

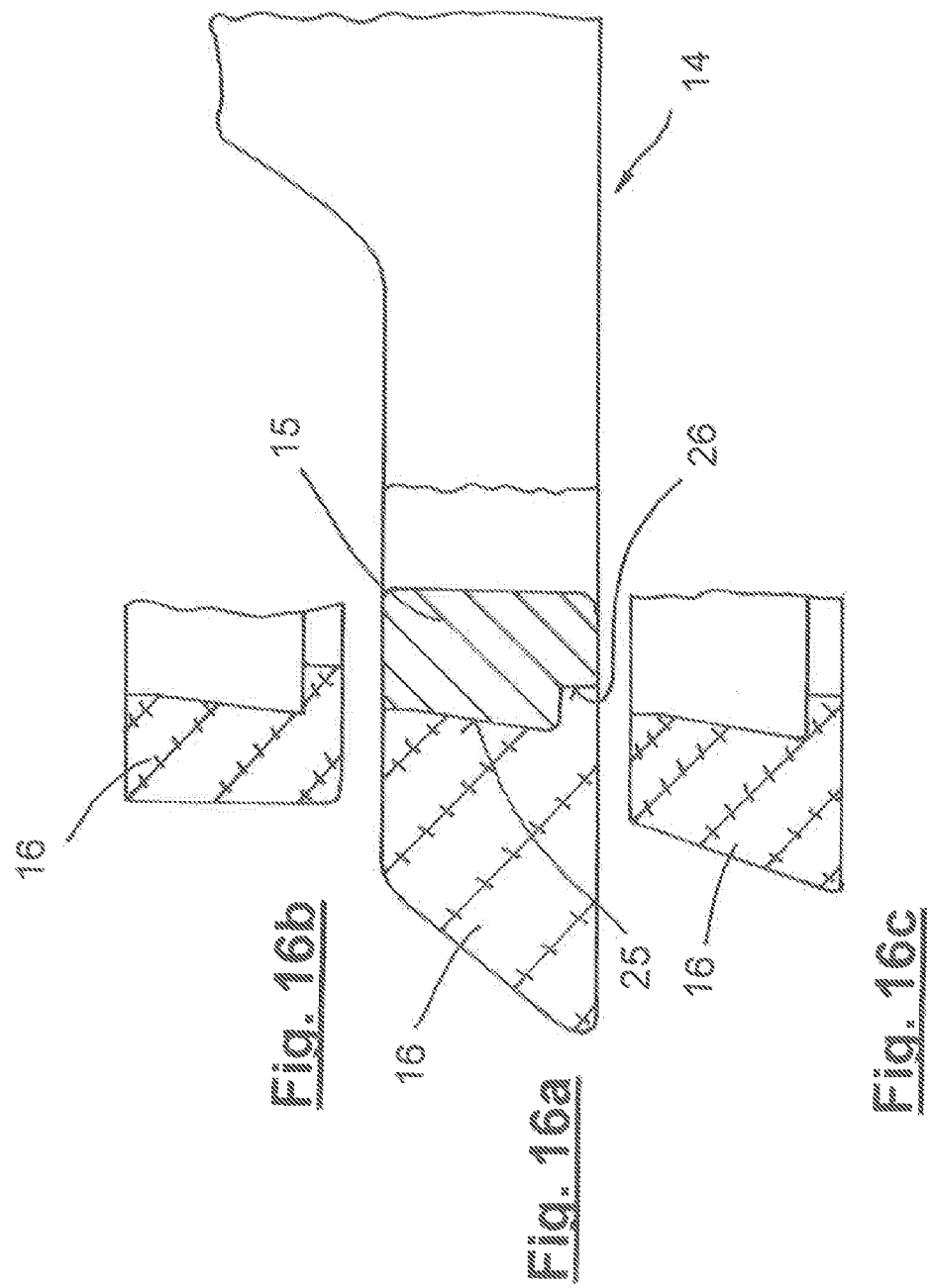

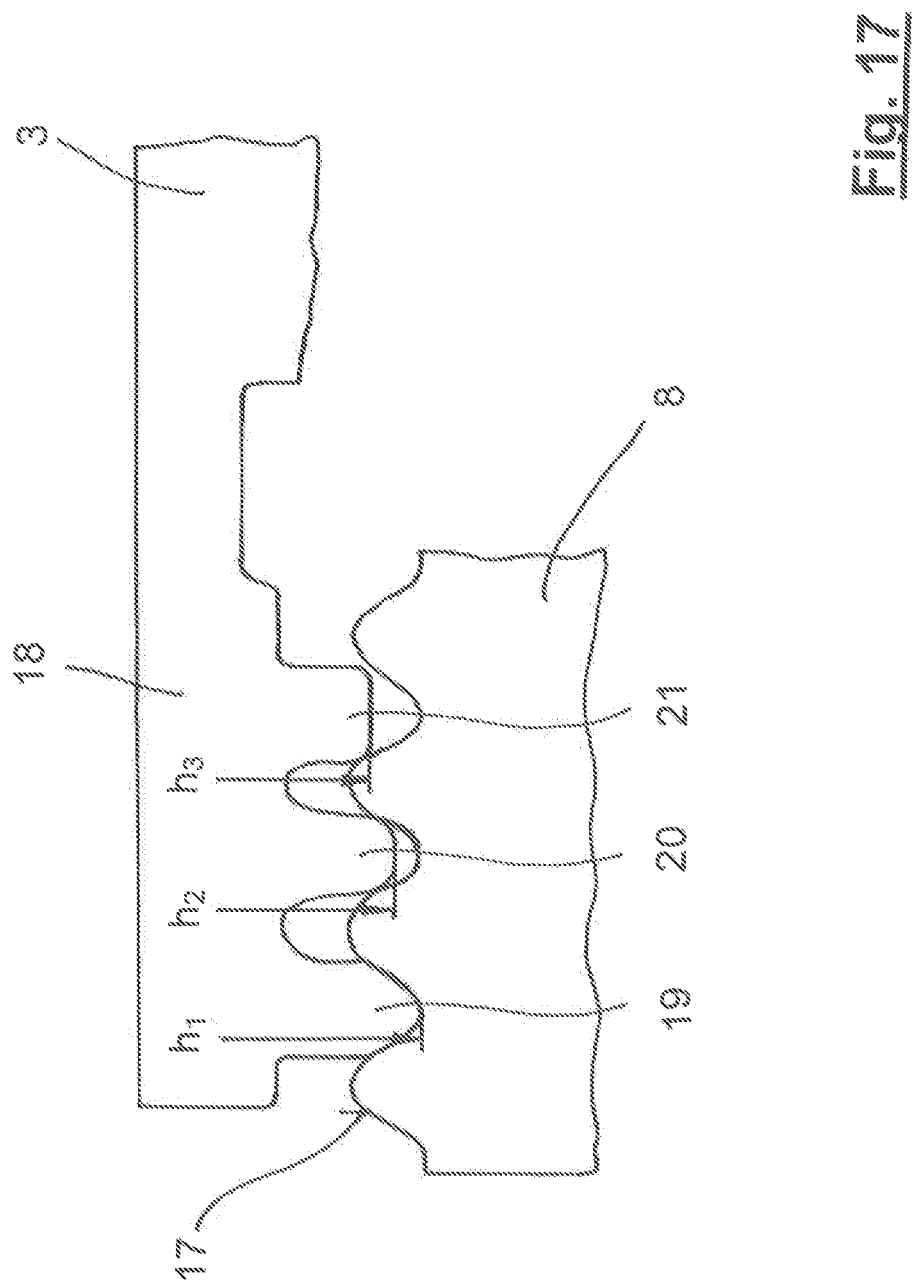

ELECTRODE ARRANGEMENT

Figure 1:
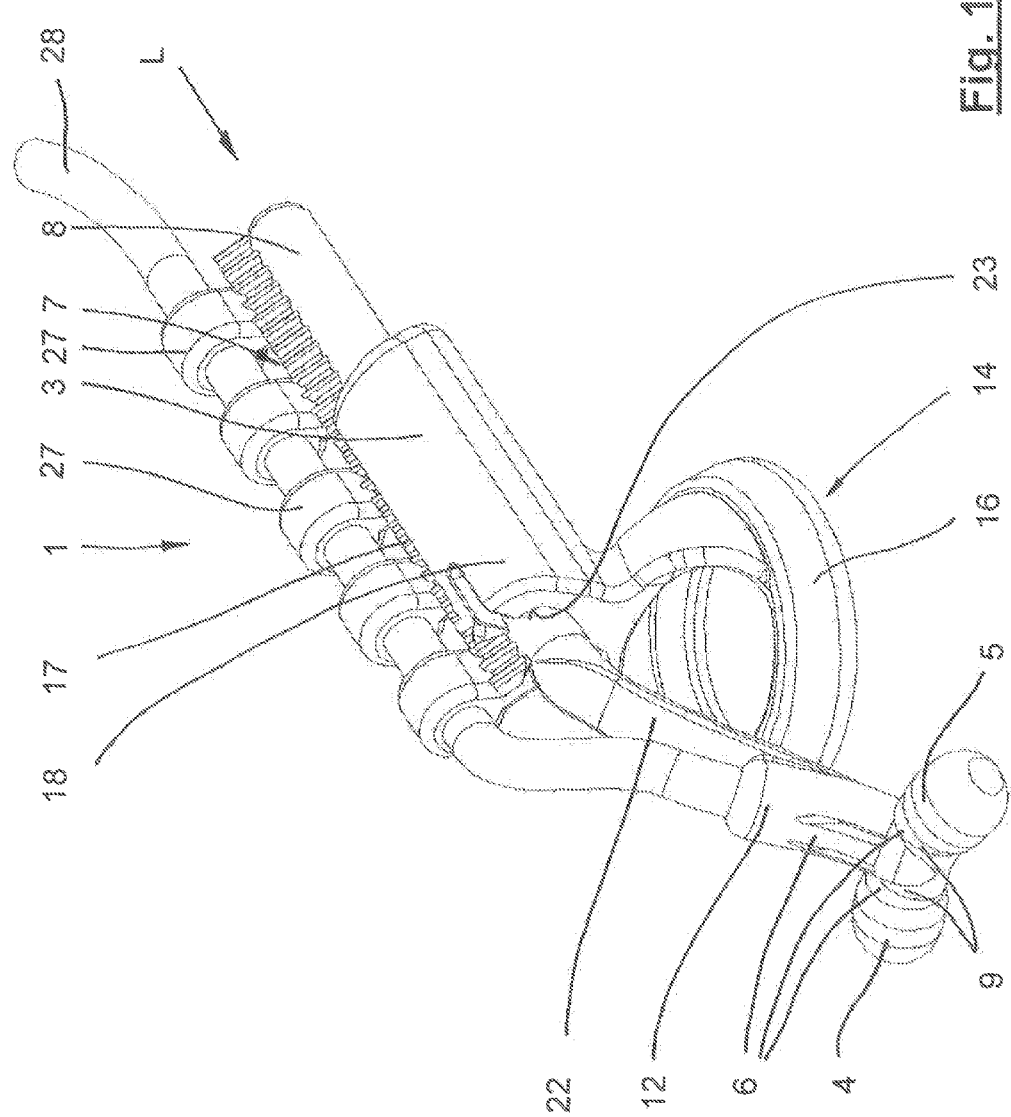

This application claims priority under 35 USC 119 and incorporates by reference the following applications: U.S. Provisional Application No. 61/681,198 filed Aug. 9, 2012; German Application No. 10 2012 014 764.3 filed Jul. 25, 2012, published as DE 10 2012 014 764A1; and German Application No. 10 2012 004 021.0 filed Mar. 2, 2012, abandoned.

The invention relates to an electrode arrangement for applying of a transcutaneous electrical stimulation stimulus onto the surface of a section of the human ear, which comprises a holding element to be attached at or in the ear as well as at least one electrode, which electrode is arranged in or at an electrode carrier, wherein the holding element comprises a linear guide in which a supporting rod is arranged linear movable in the direction of a longitudinal axis of the holding element and wherein the electrode carrier is arranged at the supporting rod.

It is generally known to take influence on the neurophysiological and neuroelectrical quality through invasive and non-invasive stimulation of the nerves and thereby on the function of the simulated nerves. Hereby different conditions of sickness can be treated. Numerous devices exist both for the invasive and the non-invasive stimulation.

The present invention is based upon the method of the transcutaneous electrical stimulation of the nerves. At this method pulse currents of different current forms, amplitudes, pulse durations and frequencies are administered through the skin on different nerves and change their status parameter in an advantageous way.

An electrode arrangement of the kind which is mentioned at the beginning is known from the EP 2 026 872 B1, patented. An electrode arrangement is described here which comprises a housing, which is entirely placeable within the pinna. From the housing two bent, wire-like sections are extending, wherein they are formed as spring-elastic carriers. Therewith the electrode arrangement can be put into the needed position by a slight clamping in the pinna, so that the ear canal can be charged with a transcutaneous stimulus. Other stimulation devices are disclosed in DE 10 2005 003 735 A1, patented as DE 10 2005 003 725 B4, and U.S. Pat. No. 5,514,175.

Even though the pre-known electrode arrangement already leads to good treatment results, certain drawbacks turned out during the practical experience.

Due to natural condition that the electrode arrangements with their electrodes have to be built very small, the mechanical stability of the required connections is not solved yet in an ideal way, particularly of the electrodes with their cable connections. Therefore it can come to an insufficient support of the electrodes, which is promoted by the fact, that a very soft cuddly material (especially silicon) has to be employed for the holding to achieve a sufficient wearing comfort. With a respective mechanical strain of the electrode arrangement it comes occasionally to irreparable damages at the contacts of the electrodes while inserting them into the ear canal.

In addition it has been recognized as disadvantageous that it is difficult to adjust, if necessary, a present electrode arrangement to the individual size of the pinna respectively the ear in general. This leads occasionally to a high complexity or respectively to a not ideal wearing comfort during inserting of the electrode arrangement.

It is furthermore disadvantageous at some pre-known electrode arrangements that the hearing can be influenced negatively.

In addition, the quality of the contact of the electrodes is occasionally not ideal, because the areas of the skin, which are acquired from the electrodes, are not big enough. With some of the pre-known solutions this results from the way, how the electrodes are arranged on a carrier element.

Furthermore it is desired to provide measures to enable an adjustment of the stimulus device to an individual ear with a simple and competitive manner, despite the standardization of the stimulus devices.

Thus, it is an object of the invention to develop an electrode arrangement of the generic kind in such a way to stay abreast of the mentioned disadvantage. Thus, an electrode arrangement shall be proposed which allows the disposing of the electrode arrangement in an easy and convenient manner. Thereby, the hearing should be influenced as little as possible negatively during wearing of the electrode arrangement. The contact quality of the electrodes should be improved by an optimized design.

The solution of this object by the invention is characterized in that the electrode carrier comprises at least one carrier section on which the electrode is arranged, wherein the electrode comprises at least one cylindrical and/or spherical segment shaped and/or conical surface section.

Thereby a cylindrical and a spherical segment shaped surface section or a conical shaped and a segment shaped surface section is preferably provided.

A preferred solution provides, that the electrode in its area, which is facing the carrier section, is formed cylindrically, wherein a spherical segment shaped section attaches to the cylindrical area of the electrode, which end area is averted from the carrier section. With this solution it can be provided moreover, that the transition of the electrode from its cylindrical region to the carrier section is formed by a conical region, wherein the cylindrical region has a bigger diameter than that one of the carrier section.

The electrode carrier can thereby comprises a holding section which comes from the supporting rod, on which end at least two carrier sections pointing into different directions are arranged with the respective electrodes.

The at least one carrier sections can comprise an axle element on which the electrode is applied, particularly is plugged on. The electrode on the axle element can be attached adhesive bonded, form-fitted and/or can be fictionally engaged.

An alternative solution provides that the at least one carrier sections, preferably together with the holding section, is formed by an injection molding process, wherein the electrode is connected with the carrier section in situ by the injection moulding process.

The holding section can comprise a longitudinal axis which encloses an angle to the longitudinal axis of the holding section, which is between 20° and 80°, preferably between 40° and 70°.

A preferred embodiment of the invention provides that (exactly) two carrier sections and/or axle elements are provided, which are arranged below an angle, which is between 140° and 180°, preferably between 165° and 175°.

Furthermore it can be provided, that the holding element comprises a resting part, that is designed and provided for resting in the Cavum conchae of the ear.

The electrode carrier is mostly arranged to an axial end of the supporting rod.

The electrode carrier comprises preferably at least one stimulation electrode and at least one reference electrode, particularly shaped as an electrode head.

The linear guide of the holding element can be built by a recess, which comprises an even form, particularly a circular form, in a section that is perpendicular to the longitudinal axis along the longitudinal axis; then, the supporting rod comprises preferably a circular profile at least along a part of its extension.

Additionally or alternatively fixation means can also be provided, which block the relative linear position between the supporting element and the supporting rod, i.e. which prevent the linear shift by the linear guide.

Furthermore spring means can be arranged between the linear guide and the supporting rod so that the supporting rod can be elastically biased relative to the linear guide in direction to the longitudinal axis.

In general it can be provided, that a desired flexibility of the electrode carrier will be reached relatively to the holding element through relevant methods. The mentioned integration of a spring element is just a possibility here. Through adequate constructive methods it can be achieved that the flexibility respectively the spring constant lies within a desired region. In doing so it is possible for example, to enforce a section of the supporting rod through a metallic flat spring and at the same time to take back the material of the supporting rod in this region or to do entirely without it. The flat spring enables a spring flexibility into a defined direction while the connection between the holding element and the electrode carrier stays firmer in other load directions.

From the above mentioned information it is understandable, that the definition of the "supporting rod" is to be interpreted broadly and does not limits itself only to classical rod formed structures.

In its axial end region where the electrode carrier is arranged, the supporting, rod can comprise furthermore at least one collateral housing or at least one collateral cut to reduce the bending stiffness of the supporting rod in a direction perpendicular to the longitudinal direction within the axial end region. The adjustment of the electrode carrier to the topography surface of the skin which is to be stimulated will be thereby facilitated.

The ring shaped section of the resting part can comprise an interruption at at least one location of the circumference. Thereby it can be achieved that a simplified adjustment of the circular ring shaped section is given to the resting area within the ear at different ear sizes.

The parts of the electrode arrangement consist preferably of a soft material—as far as the contact to the skin is given—, wherein it is specifically thought of are elastomere material, especially at silicon or a material, which comprises silicon. Meanwhile the electrode head and the supporting rod consist preferably of a thermoplastic or duroplastic synthetic material, for example of polyurethane.

It shall be mentioned, that the suggested electrode arrangement can also comprise only one electrode. It is possible that a separate reference electrode will be employed, which will be placed outside of the electrode arrangement (e.g. behind the ear) and which is in electrical connection to the simulation device. It is also possible that indeed two or more electrodes exist—like in the demonstration example—but that a further reference electrode can be employed outside of the electrode arrangement.

A further embodiment provides that the electrode arrangement is supplied with an acoustic transmitter (loud speaker), preferably in the region of the resting, part respectively of its ring shaped section. Thereby it will be possible to feed the user also with acoustical signals during the electro stimulation, which can also happen for entertainment purposes.

It is beneficial that a quite stable construction can be reached through the suggested embodiment of the electrode arrangement without influencing the wearing comfort negatively. The electrodes will be kept stable and reliable in the necessary position as they are arranged via the supporting rod at the relative stable holding element.

Through the dyadic construction it is by the way possible to combine the supporting rod including the electrode head at the one side with the holding element on the other side. This opens the possibility to combine different sized elements with each other. A preferred delivered embodiment provides therefore more than one supporting rod including the electrode head and/or more than a holding element. The user can then choose and join the elements according to the ideal size of his proportions to have an ideal fitting electrode arrangement in disposal.

In particular the holding elements can be adjusted therefore to different sized ears respectively different ear forms in an easy way. The electrode head respectively the electrodes lay therefore always upon the skin with a defined pressure.

Figure 10:
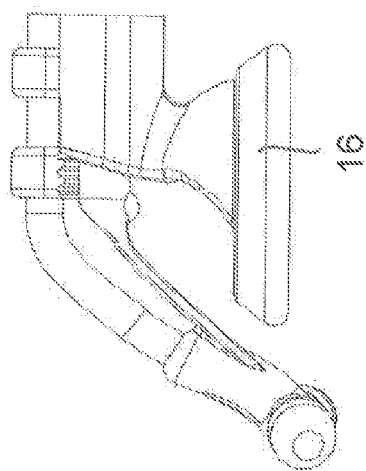
Figure 9:
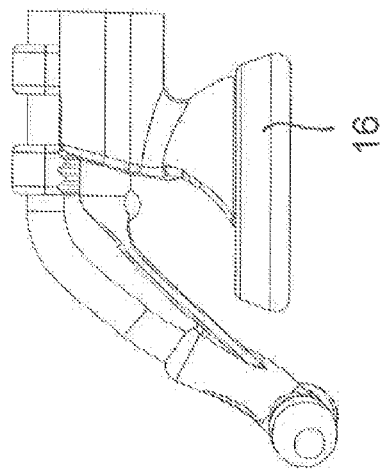
Figure 8:
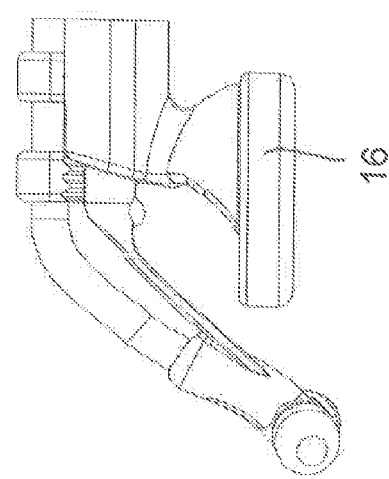
Figure 11:
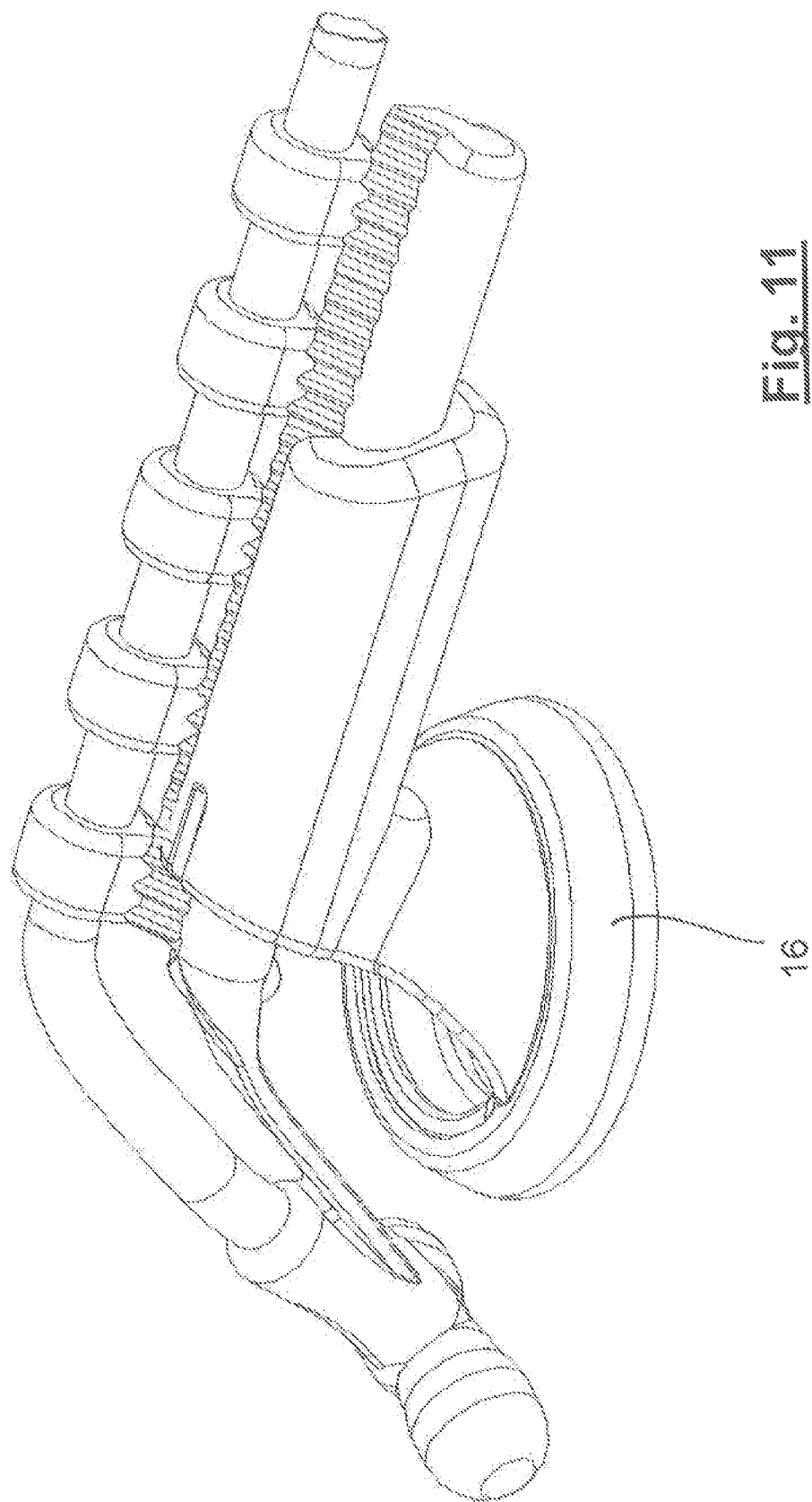
Figure 12:
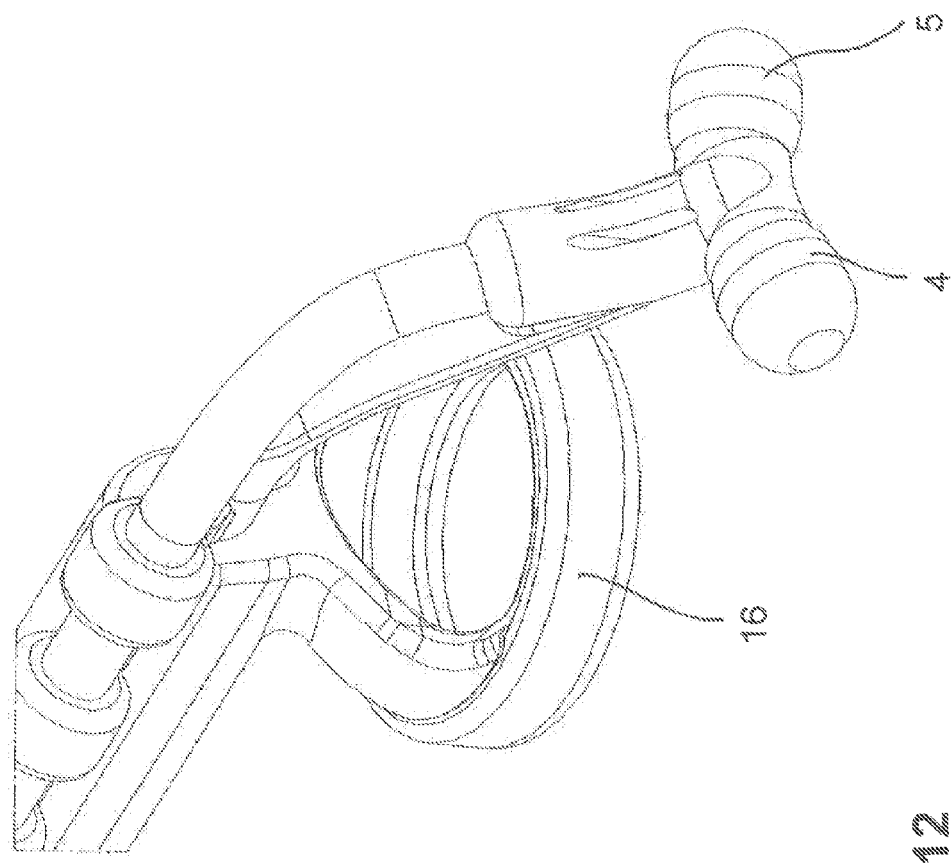
Figure 13:
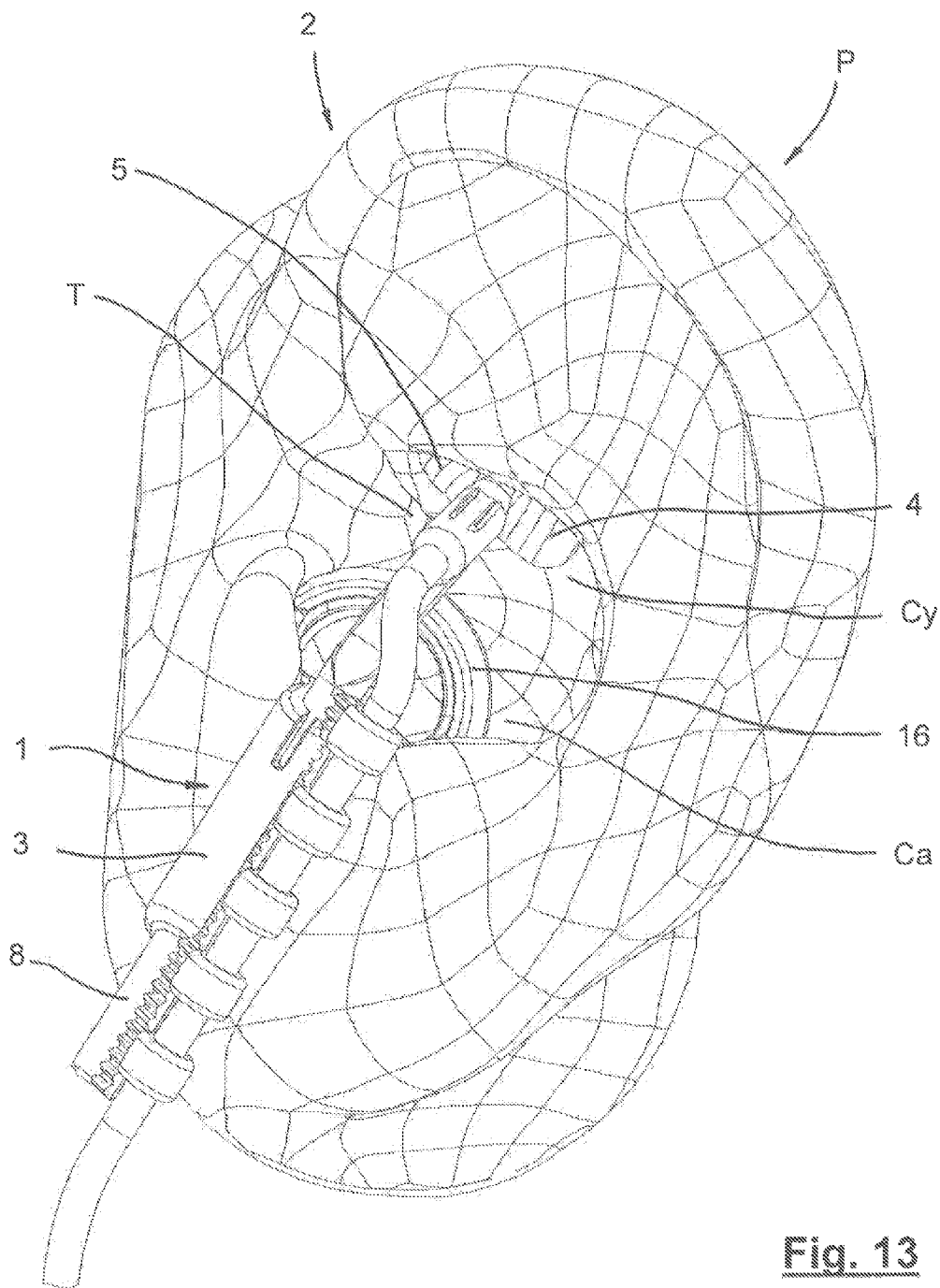
Figure 14:
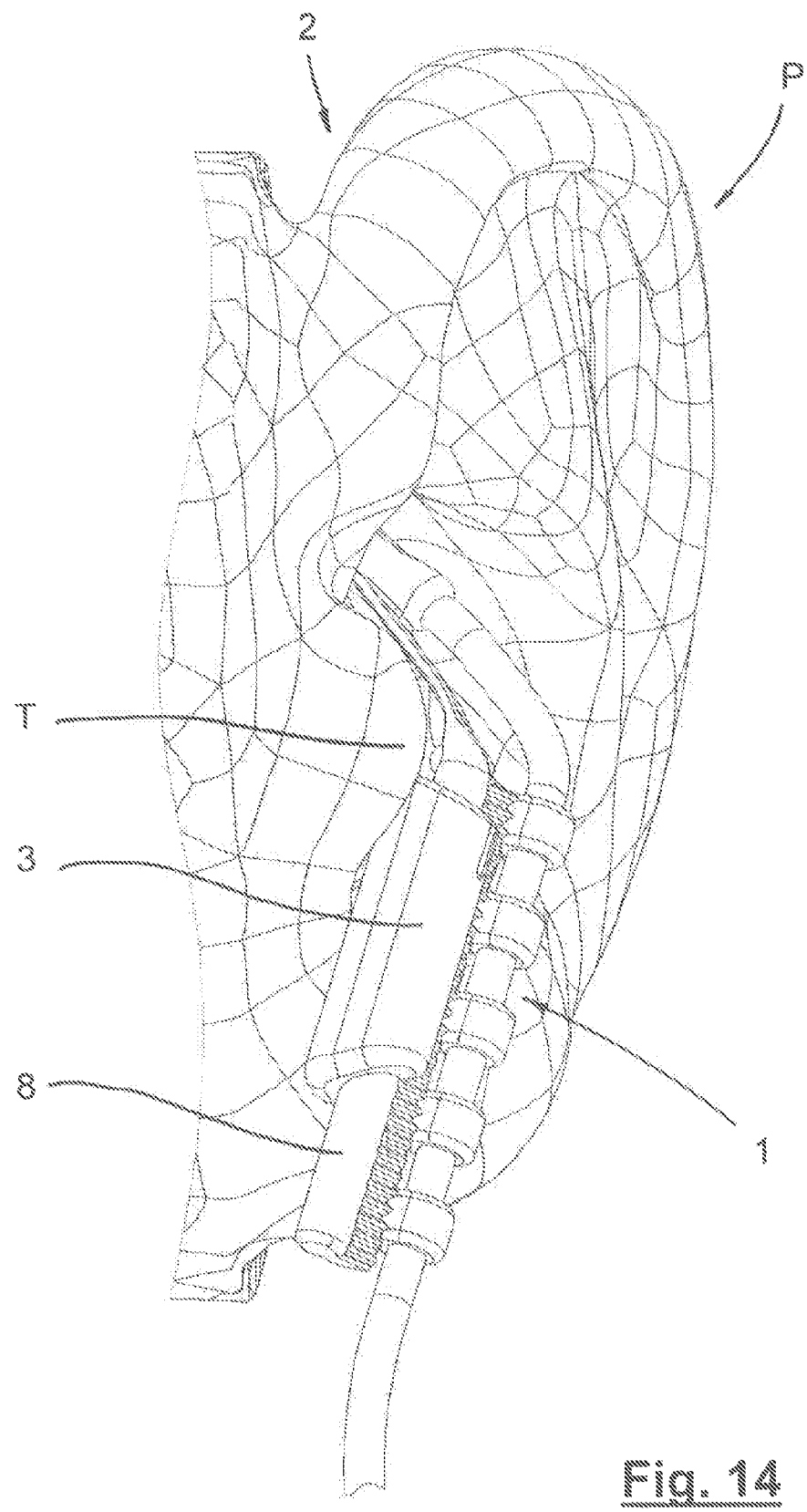

In the drawings embodiments of the invention are depicted. It shows:

FIG. 1 in a perspective view an electrode arrangement according to the invention, FIG. 2 the electrode arrangement according to FIG. 1 seen in a front view, FIG. 3 in a perspective view an electrode arrangement according to FIG. 1, looking at it from underneath, FIG. 4 in a top view the front section of the electrode arrangement according to FIG. 1, FIG. 5 the electrode arrangement according to FIG. 1, seen in a front view, FIG. 6 in a perspective view the front section of the electrode arrangement according to FIG. 1, wherein the electrodes themselves are demounted, FIG. 7 the side view of the front section of the electrode arrangement according to FIG. 1, FIG. 8 the side view of the front half of the electrode arrangement according to FIG. 1 with a first embodiment of a ring shaped contact element, FIG. 9 the side view of the front half of the electrode arrangement according to FIG. 1 with a second embodiment of a ring shaped contact element, FIG. 10 the side view of the front half of the electrode arrangement according to FIG. 1 with a third embodiment of a ring shaped contact element, FIG. 11 in a perspective view the electrode arrangement according to FIG. 1, FIG. 12 in a perspective view the front part of the electrode arrangement according to FIG. 1, seen from another direction, FIG. 13 the view of an oar with an electrode arrangement, which is inserted into the ear, FIG. 14 the depiction according to FIG. 13, seen from another direction, FIG. 15 the side view of the electrode arrangement according to FIG. 1, FIG. 16*a* a partial sectional view of a resting part of the electrode arrangement with a ring shaped contact element according to a first embodiment, FIG. 16*b* a sectional view of the ring shaped contact element according to a second embodiment, FIG. 16*c* a sectional view of the ring shaped contact element according to a third embodiment and FIG. 17 a schematically side view of latching means, which are arranged effectively between a holding element and a supporting rod of the electrode arrangement.

In FIG. 1 an electrode arrangement 1 is depicted in form of an otoplastic, which can be inserted into a human ear 2 which is depicted in FIG. 13 and FIG. 14 respectively, to conduct a transcutaneous electrical stimulation of the skin surface in the region of the ear.

With the electrode arrangement 1 a transcutaneous electrical stimulation of the nerves can be conducted precisely upon a surface region of the ear. For this purpose the electrode arrangement comprises a stimulation electrode and a reference electrode (s. below), between which an electrical potential is produced; the therefore needed means are sufficiently known from the state of the art, so that they won't have to be described any further here. It is referred exemplarily and explicitly to DE 10 2005 003 735 B4, patent of the applicant.

The electrode arrangement 1 has a holding element 3 as well as a supporting rod 8 as essential construction components. The supporting rod 8 carries at one of its axial ends via a connection element 22 an electrode carrier 6 which is equipped with two electrodes 4, 5, that is to say with a stimulation electrode 4 and a (identically constructed) reference electrode 5. The electrode carrier 6 holds both electrodes 4, 5 on a desired distance and is shaped as a bridge element between the electrodes 4, 5. The holding element 3 has a central section which is dominated from a linear guide 7 which is built out of sections of the parts 3 and 8. In this connection it is about a material section that extends itself in a longitudinal direction L with a form such as a rod, in which a circular recess 23 is molded.

A resting part 14 is formed at the frontal end of the holding element 3. The resting part 14 comprises a ring shaped section 15 (s. particularly FIG. 16). The ring shaped section 15 is surrounded by a ring shaped contact element 16 which consist of a soft synthetic material and which lies upon the surface of the skin, as it results out of FIG. 13.

It is thereby essential that the holding element 3 is able to move the supporting rod 8 linear into the direction of the longitudinal axis L by the linear guide 7.

Therewith it will be possible to change the distance between the electrode carrier 6 and hence the electrodes 4, 5 and particularly the resting part 14 and to adjust it to a desired degree.

This possibility of adjustment is used to adjust the electrode arrangement after placing into the ear 2 in such a way that they find a flexible hold in the ear 2 at a good carrying comfort.

For this it is referred to FIG. 13 and FIG. 14. Here it can be seen, that the electrode arrangement 1 has been inserted into the ear 2 and by linear displacement of the supporting rod 8 relatively to the holding element 3 has been adjusted in such a way, so that the electrode arrangement 1 has clamped elastically due to the topography of the ear 2. The electrode arrangement 1 has been arranged practically in the pinna P of the ear 2 in such a way that the electrode carrier 6 comes to lie within the region of the Cymba conchae Cy while the resting part 14 with its ring shaped contact element 16 is borne on the region of the Cavum conchae Ca. Accordingly the ring shaped contact element 16 comes to lie below the tragus T.

As a result of a (due to the material) spring flexibility of the supporting rod 8 respectively because of a spring element which is integrated into the supporting rod 8 if needed (e.g. spring wire) the electrode arrangement 1 clamps itself therefore relative elastically to the holding element 3 after the appropriate linear placement of the supporting rod 8, so that a sufficient support is given within the ear. As shown in FIG. 13, the ring shaped embodiment of the ring shaped contact element 14 allows an extensively undisturbed hearing sensation.

As further can be seen in FIG. 1, the supporting rod 8 is not twistable around the longitudinal axis L relatively to the holding element 3 due to its forming. This will be achieved by a rack shaped contour 17 which is formed onto the supporting rod 8 and which extends into a recess which extends radially from the circular recess 23 of the holding element 3. A section of the holding element 3 is shaped furthermore as engagement element 18 (s. FIG. 17), wherein a latching means are formed by the rack shaped contour 17 on the one side and the engagement element 18 on the other side, by which the supporting rod 8 can be shifted relative to the holding element 3 in a rattling way, i.e. stepwise linear into the direction of the longitudinal axis L.

An essential aspect of the present invention is the design of the electrodes 4, 5 on the electrode carrier 6. As it can be best seen in FIG. 2, the electrodes 4, 5 have a design, which is composed form a cylindrical section 10 and a spherical segment shaped section 11. Also conical shaped sections can be provided additively or alternatively. By that it will be achieved that the electrodes—depending from the pressure—acquire relatively big skin contact areas, i.e. having a big contact surface of the skin, which accordingly promotes the transcutaneous stimulation. The electrodes 4, 5 are shaped in accordance with this anyhow ellipsoid or pearl shaped at least in sections. In an advantageous way this gives an improved adjustment of the electrodes to the given anatomy of the ear.

A possible attachment of the electrodes 4, 5 on the electrode carrier 6 arise from the FIGS. 3 to 7. Accordingly, the electrode carrier 6 comprises a holding section 12 on which two carrier sections 9 are arranged. Each carrier section 9 has an axle element 13—s. FIG. 6—on which one electrode 4, 5 can be plugged on. Hereunto the electrode 4, 5 comprises a corresponding bore 24 (s. FIG. 7), so that after attaching the electrodes 4, 5 on the axle elements 13 according to FIG. 6 the arrangement results, how it can be seen in FIGS. 3, 4, 5 and 7.

in this connection it is to say, that both carrier sections 9 respectively axle elements 13 which are shown for example in FIGS. 4, 5 and 6 are arranged in an angle just below 180°—in the demonstration example it is ca, 170°—which opens itself to the skin, so that an ideal rest of the electrodes on the skin is assured. Asforesaid angle is named in the FIGS. 4 and 6 with β.

The electrodes 4, 5 can be glued on the axle elements 13 for example.

An alternative solution provides that the electrodes 4, 5 are injected during the injection molding of the electrode carrier 6 including the carrier sections 9. Then, the electrodes are therefore beneficially not insert molded, but are arranged on a synthetic core. So, the arrangement of the electrodes is optimized for the intended purpose.

From the synopsis of FIGS. 8 to 12 and 16 a further and very advantageous embodiment of the invention becomes apparent: The resting part 14 consists of a ring shaped section 15, which is surrounded by a detachable ring-shaped contact element 16. Thereby, for the contact element 16 which consists of a soft material several forms are possible, as they are recognizable from FIGS. 8, 9 and 10 and analog also from FIGS. 16a, 16b and 16c, where the respective sectional views are shown.

The form of the ring shaped section 15 is congruent to the form of the ring shaped contact element 16. A slight conical form 25 of the radial outer area of the ring shaped section 15 is provided, also a recess 26 in the ring shaped section 15 is provided. The ring shaped contact element 16 is formed congruently for this so that it can be slide on the ring shaped section 15 with undercut and therefore finds here sufficient hold.

In FIG. 15 it is recognizable that the holding section 12 of the electrode carrier 6 comprises a longitudinal axis M, which cuts the longitudinal axis L under an angle α which is ca. 65° in the embodiment. With that the electrodes are arranged in an acute angle to the contact surface.

As in FIG. 17 further can be seen, the engagement element 18 forms a free section of the holding element 3, which is created by cuts into the material of the holding element and is therefore held flexible. At the side facing the rack shaped contour 17 three teeth 19, 20 and 21 are formed on at the engagement element 18. These are arranged staggered in regard to their height (s. the heights $h_1$, $h_2$ and $h_3$) so that the latching function is determined primary from the tooth 19 and that only by support from the teeth 20 and 21.

At the radially exterior end of the section with the rack shaped contour 17 of the supporting rod 8 several holding means 27 in form of ring shaped structures are formed, which serve for that reason, to hold a cable 28 (preferably with 3-lead Kevlar wire and surrounded by bio-compatible casing material) strain-relieved, which supplies the electrodes 4, 5 with electricity. Thus, the holding means 27 serve for cable leading loops in which the cable 28 is led and strain-relieved, in doing so the cable 28 can be insert moulded also during the injection molding of the pieces 8, 17 and 27 which are made in one piece. At the manufacturing of the electrode carrier 6 by injection moulding the cable 28 can also be insert moulded in an analog way, to achieve a hermetic sealing of all joints.

At the supporting rod 8 a connection element 22 connects itself—as a connection section to the electrode carrier 6—, which has the function to lead the electrode carrier 6 down from the height, in where the linear guide 7 is arranged, to the skin surface which is to be stimulated. As already mentioned this has to be carried out so that the electrode carrier 6 presses elastically against the skin surface and preferably creates incidentally also a pre-load into the direction of the longitudinal axis L.

For this purpose it will be accessed to a material for the connection element 22, which comprises the desired flexibility; thus, this element has preferably spring elastic characteristics. It is also possible that the connection element 22 integrates a spring element. In this connection it can be for example a spring wire, which is insert moulded during the injection moulding of the supporting rod 8 including the connection element 22. As for example recognizable from FIG. 1, the connection element 22 is not ring shaped in the cross section but shaped flattened. Herewith the flexibility of the electrode carrier 6 increases into a direction which is perpendicular to the longitudinal axis L.

At that point the material will be chosen, if necessary the integration of a spring element and the geometrical form of the supporting rod in such a professional way that a desired flexibility is at hand.

LIST OF REFERENCES

1 Electrode Arrangement
2 Ear
3 Holding element
4 Electrode (stimulation electrode)
5 Electrode (reference electrode)
6 Electrode carrier
7 Linear guide
8 Supporting rod
9 Carrier section.
10 Cylindrical section of the electrode
11 Spherical segment shaped section of the electrode
12 Holding section
13 Axle element
14 Resting part
15 Ring shaped section
16 Ring shaped contact element
17, 18 Latching means
17 rack shaped contour/wave shaped contour
18 Engagement element
19 Tooth
20 Tooth
21 Tooth
22 Connection element
23 Circular recess
24 Bore
25 Conical form
26 Recess
27 Holding means
28 Cable
L Longitudinal axis
M Longitudinal axis of the holding section
α Angle
β Angle
Ca Cavum conchae
Cy Cymba conchae
T Tragus
P Pinna

The invention claimed is:

1. An electrode arrangement for applying of a transcutaneous electrical stimulation stimulus onto the surface of a section of the human ear, which comprises a holding element to be attached at or in the ear as well as at least one electrode, which electrode is arranged in or at an electrode carrier, wherein the holding element comprises a linear guide in which a supporting rod is arranged to be linearly movable in the direction of a longitudinal axis of the holding element and wherein the electrode carrier is arranged at the supporting rod,
wherein:
 at least a portion of the holding element is adapted to rest in a Cavum conchae of the human ear;
 the at least one electrode is adapted to fit within a pinna of the human ear; and
 the electrode carrier is adapting to be disposed within a Cymba conchae region of the human ear;
 wherein
 the electrode carrier comprises at least one carrier section on which the electrode is arranged, wherein the electrode comprises at least one of a cylindrical shaped segment, a spherical shaped segment, and a conical surface section.

2. The electrode arrangement according to claim 1, wherein the electrode is designed cylindrical in its section facing the carrier section, wherein a spherical segment shaped section adjoins to the cylindrical region of the electrode in its end remote from the carrier section.

3. The electrode arrangement of claim 2, wherein the transition of the electrode from its cylindrical region to the carrier section is formed by a conical region, wherein the cylindrical region has a bigger diameter than that one of the carrier section.

4. The electrode arrangement of claim 1, wherein the electrode carrier comprises a holding section which comes from the supporting rod, on which end at least two carrier sections pointing into different directions are arranged with the respective electrodes.

5. The electrode arrangement of claim 1, wherein the at least one carrier sections comprises an axle element on which the electrode is applied, particularly is plugged on.

6. The electrode arrangement of claim 5, wherein the electrode on the axle element is attached adhesive bonded, form-fitted and/or is fictionally engaged.

7. The electrode arrangement of claim 1, wherein the at least one carrier sections, is formed by an injection molding process, wherein the electrode is connected with the carrier section in situ by the injection moulding process.

8. The electrode arrangement of claim 1, wherein the holding section comprises a longitudinal axis (M), which encloses an angle ($\alpha$) to the longitudinal axis (L) of the holding section, which is 20° to 80°.

9. The electrode arrangement of claim 1, wherein two carrier sections and/or axle elements are provided, which are arranged below an angle ($\beta$), which is 140° to 180°.

10. The electrode arrangement of claim 1, wherein the holding element comprises a resting part, that is designed and provided for resting in the Cavum conchae (Ca) of the ear.

11. The electrode arrangement of claim 7, wherein the at least one carrier section and the holding section are formed together by the injection molding process.

12. The electrode arrangement of claim 8, wherein the angle ($\alpha$) is 40° to 70°.

13. The electrode arrangement of claim 9, wherein the angle ($\beta$) is 165° to 175°.

* * * * *